(12) United States Patent
Brennan et al.

(10) Patent No.: US 6,337,393 B1
(45) Date of Patent: *Jan. 8, 2002

(54) METHOD AND COMPOSITION FOR CHEMICAL SYNTHESIS ON AN OPEN ENVIRONMENT SUPPORT SURFACE USING HIGH BOILING POINT ORGANIC SOLVENTS TO CONTROL EVAPORATION

(75) Inventors: Thomas M. Brennan, San Francisco; Albrecht W. Frauendorf, Union City, both of CA (US)

(73) Assignee: Protogene Laboratories, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/662,066

(22) Filed: Sep. 14, 2000

Related U.S. Application Data

(63) Continuation of application No. 08/970,115, filed on Nov. 13, 1997, now Pat. No. 6,177,558.

(51) Int. Cl.$^7$ ............................................... C07H 21/00
(52) U.S. Cl. .................... 536/25.3; 536/22.1; 536/23.1; 536/24.1; 536/24.3; 536/25.31; 536/25.33; 536/25.4; 536/25.41; 435/6; 435/91.1; 435/810; 436/501
(58) Field of Search ............................... 536/22.1, 23.1, 536/24.1, 23.3, 25.33, 24.3, 26.31, 25.4; 435/6, 91.1, 810; 436/501

(56) References Cited

U.S. PATENT DOCUMENTS

| 5,003,059 A | 3/1991 | Brennan |
| 6,028,189 A | 2/2000 | Blanchard |
| 6,177,558 B1 * | 1/2001 | Brennan et al. |

FOREIGN PATENT DOCUMENTS

| EP | 0 373 203 B1 | 8/1994 |
| EP | 0 703 825 B1 | 7/1997 |
| WO | WO 90/03382 | 4/1990 |
| WO | WO 94/03530 | 2/1994 |
| WO | WO 94 27719 A | 12/1994 |
| WO | WO 95/11262 | 4/1995 |
| WO | WO 95/23163 | 8/1995 |
| WO | WO 95 25116 A | 9/1995 |
| WO | WO 95/32980 | 12/1995 |
| WO | WO 95/35505 | 12/1995 |
| WO | WO 97/19749 | 6/1997 |
| WO | WO 97/44134 | 11/1997 |
| WO | WO 98 25944 A | 9/1998 |
| WO | WO 98 41531 A | 9/1998 |

OTHER PUBLICATIONS

Brown, T., et al., "Modern machine–aided methods of oligodeoxyribonucleotide synthesis", Oligonucleotides and Analogues a Practical Approach—pp. 1–24 (1991).

Feiser & Feiser, "Reagents for Organic Synthesis", Wiley 1:1109–1111 (1967).

Gryaznov, S.M., et al., "Selective O'phosphitilation with nucleoside phosphoramidite reagents", *Nucleic Acids Research* 20(8):1879–1882 (1992).

Lemmo, A. V. et al., "Characterization of an inkjet chemical microdispenser for combinatorial library synthesis", *Analytical Chemistry* 69(4):543–551 (1997).

O'Donnell–Maloney M. J. et al, "Microfabrication and array technologies for DNA sequencing and diagnostics", *Genetic Analysis: Biomolecular Engineering* 13 (6):151–157 (1996).

Ono, A., et al., "The synthesis of blocked triplet–phosphoramidites and their use in mutagennesis", *Nucleic Acids Research* 23(22) (1995).

* cited by examiner

Primary Examiner—James O. Wilson
(74) Attorney, Agent, or Firm—Albert P. Halluin; Wallace Wu; Howrey Simon Arnold & White, LLP

(57) ABSTRACT

A method for reducing evaporation of a liquid reagent solution during solid phase, micro-scale chemical synthesis of a molecule comprising sub-units on an open environment solid support surface. The method includes the steps of providing an open solid support surface including at least one binding site which is functionalized with a reactive chemical moiety; and depositing a substantially controlled and minute volume of liquid reagent solution onto the support surface, and in contact with the binding site. The reagent solution includes reactants contained in at least one relatively high boiling point solvent, in contrast to standard organic solvents for such reagents. Application of a high boiling point solvent substantially reduces evaporation of the reagent solution in the open environment during synthesis on the solid support while enabling the maintenance of a substantially high reaction yield.

35 Claims, 2 Drawing Sheets

METHOD AND COMPOSITION FOR CHEMICAL SYNTHESIS ON AN OPEN ENVIRONMENT SUPPORT SURFACE USING HIGH BOILING POINT ORGANIC SOLVENTS TO CONTROL EVAPORATION

This application is continuation application of U.S. Application Ser. No. 08/970,115, filed on Nov. 13, 1997 now U.S. Pat. No. 6,177,558, which is incorporated herein by reference in its entirety.

TECHNICAL FIELD

This present invention relates, generally, to chemical reactions using high boiling point organic solvents on a support surface, and, more particularly, relates to solid phase synthesis at small, open, individual reactive sites spatially separated on the support surface.

BACKGROUND ART

Determination of the sequence of DNA, RNA, and peptide fragments continues to play a significant role in the development of diagnostic medicine, forensics, molecular biology research, and pharmaceutical pharmacogenetics. However, more recently attention has turned from the determination of sequence itself to identification of the function of sequences in biochemical pathways and disease states. Because the genetic influence on most biochemical pathways has been more complex than originally thought, typically involving multiple genes, multiple mutations in genes, and complex interactions, the need to improve the productivity to perform simultaneously multiple assays of DNA sequence has grown.

One way to achieve many parallel simultaneous measurements is to lay out a large number of DNA, RNA, or peptide probe assays onto a microarray which can then be probed simultaneously by complex biological samples. Each individual probe in the array, through hybridization (specific bonding), or not, with, for example, DNA or RNA in an unknown sample, provides information about the presence or absence of sequences in the sample.

These types of assays typically test for the presence of a specific nucleic acid sequence, usually a DNA or RNA sequence, although other specific binding assays are also possible. As is well known in the field, this is accomplished by utilizing oligonucleotides synthesized with specific, predetermined sequences of interest. Typically such specific sequence is based on searches of genome or mutation databases or, for example, homology to a known or putative gene or amino acid sequence, or catalogued mutations of such sequences. The presence or absence of many sequences can then be ascertained simultaneously by hybridization under conditions which allow only perfectly or closely matching sequences to associate.

There are numerous examples of important multiple assays performed by simultaneous microarray analysis. To improve productivity in disease diagnosis, an array can be made in which 500 different probes, each one corresponding to a mutation known to cause, for example, Cystic Fibrosis, are hybridized with a patient's DNA such that, if any of the causative mutations are present, that specific feature of the array representing that mutation becomes fluorescent. In another useful example, DNA sequences corresponding to many genes whose functions are unknown are formed into a microarray. Messenger RNA prepared from both normal and diseased tissue samples can then be compared by measuring differential intensity of probe hybridization on the many different sequences corresponding to many different genes simultaneously. Those genes hybridized differently in the disease tissue compared to the normal tissue can then be implicated in the disease pathway, and assigned a function. Additionally there are numerous examples in molecular biology and pharmaceutical discovery in which the presence or absence of large number DNA sequences need to be analyzed to determine important specifics of a disease state, e.g., resistance to antibiotics, genotype indicative of severity, etc.

Finally, there are many applications in which drug/receptor interactions can be determined by tethering the candidate drugs (such as small organic molecules) or biological receptors to a microarray surface and observing the degree to which the two associate.

Thus, it is often necessary to create a large number of related, but distinct chemical features on a microarray. Synthesis of arrays of bound oligonucleotides or peptides is also generally known in the art. In one approach to parallel synthesis, known as the T-bag method or disk design, an array of individual packets or disks of solid support beads are physically sorted into four (4) amidite subsets for treatment with the selected amidite. After each packet of beads has been treated with the common reagent, the packets must again be manually resorted into the four subsets for the subsequent synthesis cycle. Such sorting and resorting becomes too burdensome and labor intensive or the preparation of large arrays of oligonucleotides.

Another array approach for the synthesis of support-bound oligonucleotides is hat of Southern et. al., U.S. Pat. No. 5,436,327, which performs the synthesis in a very narrow gap between two glass plates. Not only is this technique impractical and cumbersome in practice since a plurality of different reagents must be applied accurately specific sites on the glass surface, but this approach does not allow a continuous synthesis of oligonucleotides. Moreover, since Southern uses standard reagents for phosphoramidite synthesis, the technique needs to be performed in a closed environment to prevent rapid evaporation of the highly volatile solvents (e.g., acetonitrile and dichloromethane, as will be described in greater detail below).

One preferred approach for synthesis of arrays of oligonucleotides on open solid support surfaces is described by Brennan, U.S. Pat. No. 5,474,796, which controls delivery of specific reagents through drop-on-demand inkjet devices. Brennan provides a general method for conducting a large number of chemical reactions on a support surface where very minute volumes of solutions of chemical reactants are added to functionalized binding sites on the support surface by means of a piezo electric pump. The functional binding sites are separated from each other by the use of a non-functionalized coating material with different surface tension.

While Brennan does not specify the nature of the solvents employed with this system in order to make this open surface method applicable to general chemical synthesis, in practice, most chemical reactions are performed in highly volatile, low-boiling solvents such as acetonitrile or dichloromethane. One problem associated with using these conventional solvents in open synthesis arrangements is that when the delivered drops are too small, the solvents tend to evaporate too quickly. This is especially true with the piezo electric delivery pump devices, as applied in Brennan, since the volume of delivered drops are typically between about 20 picoliters to 2 microliters. In this minute size range, the vapor pressure and surface area to total volume ratio of the drops are so high that these standard high yield DNA synthesis solvents evaporate before reacting completely.

The rate of evaporation is a function of the surface area of the drop, and is related to $1/R^2$ (where R is the radius of the drop), i.e. the smaller the drop, the faster the rate of evaporation. At 23° C., a 100 micron droplet of acetonitrile (ACN) will evaporate in flight within 1 cm of travel. Once the solvent has evaporated, the amidite coupling reaction essentially ceases in the thick, gummy or crystalline residue.

In conventional solid phase oligonucleotide synthesis on controlled pore glass (CPG), for example, the preferred solvent for the tetrazole activated, dimethoxytrityl protected nucleotide phosphoramidite coupling step is acetonitrile. This solvent has been determined to be far superior to other common solvent types for phoshoramidite coupling, such as tetrahydrofuran, dimethoxyethane and nitromethane. Acetonitrile possesses the ideal combination of acidity, viscosity, dielectric constant solubility and other properties to promote high (>99%) yield coupling. A stepwise coupling yield less than 97% would produce a useless mixture of truncated and/or deleted products.

Acetonitrile (ACN) unfortunately has a rather low boiling point (81° C.), and drops on a support surface evaporate very quickly in an open system. The other above-indicated commonly employed solvents for DNA synthesis (i.e., tetrahydrofuran, dimethoxyethane and nitromethane) also have similar boiling points and rates of evaporation as acetonitrile. Accordingly, these solvents tend to evaporate very quickly in open synthesis systems as well.

One solution would be to deliver a rapid series of droplets of reagent to build up a larger volume for the larger diameter reaction sites. However, this technique becomes ineffective for diameters less than about 500 microns, and diameters greater than 500 microns are far too large in many array approaches Moreover, the rate of evaporation may be slowed by lowering the temperature of the solvent and reaction surface, but the rate of the coupling reaction may be severely reduced. Finally, the rate of evaporation of a drop can also be slowed by increasing the relative humidity or saturation of the head space vapor by ACN. In practice however, stable ACN humidity control is difficult to achieve, and the synthesis device tends to function as a cloud chamber.

DISCLOSURE OF INVENTION

Accordingly, it is an object of the present invention to provide a method and composition for synthesis of materials on open surfaces which substantially reduces evaporation of the reagent solvent when delivered in minute volumes thereof.

It is another object of the present invention is to provide a method and composition which maintains a substantially high reaction yield.

Another object of the present invention is to provide a method and composition of reagent solution which may be delivered through conventional drop-on-demand delivery assembly.

In accordance with the foregoing objects, the present invention provides a method of reducing evaporation of a liquid reagent solution during solid phase, micro-scale chemical synthesis of a molecule comprising sub-units on an open environment solid support surface. The method includes the steps of: (A) providing an open solid support surface including at least one binding site which is functionalized with a reactive chemical moiety; and (B) depositing a substantially controlled and minute volume of liquid reagent solution onto the support surface, and in contact with the binding site. According to the present invention, the reagent solution includes reactants contained in at least one relatively high boiling point solvent, in contrast to standard organic solvents for such reagents. Such a high boiling point solvent substantially reduces evaporation of the reagent solution in the open environment during synthesis on the solid support while maintaining a substantially high reaction yield.

In another aspect of the present invention, a method for synthesizing an array of materials on open surfaces is provided which includes the steps of: providing a substantially planar, open solid support surface containing an array functionalized binding sites. Each binding site is separated by surface tension barriers of non-reactive, hydrophobic materials. The next step includes depositing a substantially controlled and minute volume liquid reagent solution onto the support surface at each functionalized binding site for contact with at least one sub-unit of the molecule affixed to the respective binding site. Each reagent solution includes nucleoside reagents contained in a polar aprotic solvents having a boiling point of at least about 140° C. Due to the elevated boiling point, the evaporation of the minute volumes of reagent solutions are substantially reduced in an open environment during molecule growth. Further, the high coupling yield is substantially maintained.

The depositing step may be performed using drop-on-demand delivery of the reagent solution. This delivery may be provided through conventional valve delivery means or through a piezo-electric pump device, as long as the delivery volume, about 20 picoliters to about 2 microliters, is controlled and accurate. Further, the depositing step is further performed by discreet, stepwise polymer synthesis at each the binding site by the phosphoramidite method.

In yet another aspect of the present invention, a nucleoside reagent solution is provided for oligonucleotide synthesis in relatively minute volumes. The reagent solution includes a nucleotide reagent, and a polar organic, aprotic solvent having a boiling point of at least about 140° C. In the small volumes delivered, evaporation of the reagent solution in an open environment is substantially reduced during oligonucleotide growth while maintaining a substantially high coupling yield.

These aprotic solvents are preferably organic in nature and are selected from the group of dinitriles, glymes, diglymes, triglymes, dimethylformamides (DMF), hexamethyphosphorictriamides (HMPA) and trimethylphosphates. This group preferably include substantially similar acidity properties as that of an acetonitrile solution. More specifically, the group of dinitriles are selected from the group consisting essentially of malononitrile, succinonitrile, glutaronitrile and adiponitrile. However, the polar organic aprotic solvents may also be selected from the group of mononitriles such as valeronitrile and capronitrile.

BRIEF DESCRIPTION OF THE DRAWING

The assembly of the present invention has other objects and features of advantage which will be more readily apparent from the following description of the best mode of carrying out the invention and the appended claims, when taken in conjunction with the accompanying drawing, in which:

FIG. 2A illustrates that a micro-droplet reagent solution is deposited on a functionalized binding site. FIG. 2B illustrates that due to differences in wetting properties between the reagent solution and the surrounding surface, the reagent solution beads on the functionalized binding site.

BEST MODE OF CARRYING OUT THE INVENTION

Figure 1:
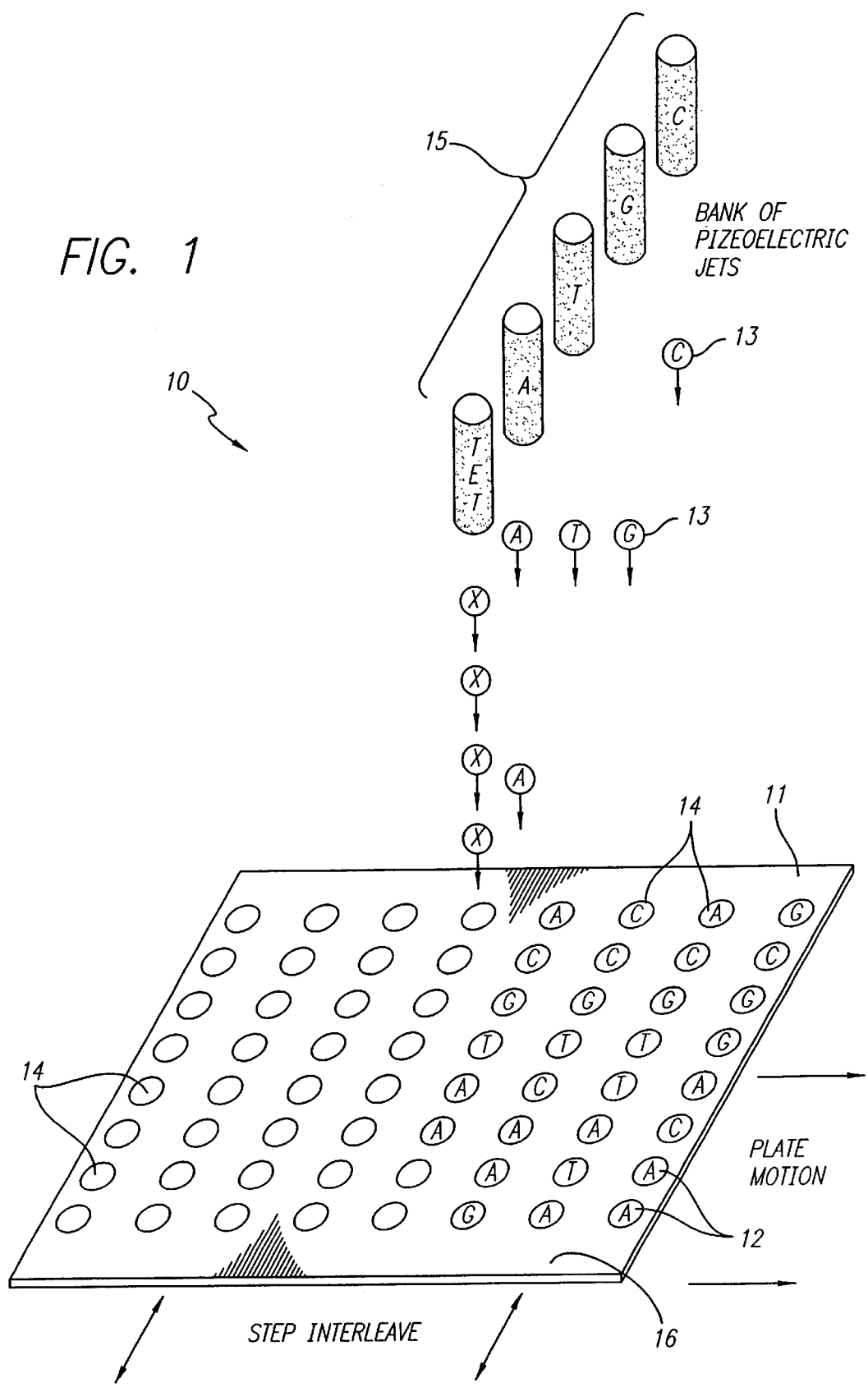
FIG. 1 is top perspective schematic view of a synthesis apparatus depositing the reagent solution of the present invention into an array of finctionalized binding sites of a support surface.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

It will further be understood that while the present invention is particularly suitable for building sequence defined oligonucleotides, the method and composition of the present invention may be employed for synthesis of any molecule comprising sub-units, and particularly sequential additional synthesis. Hence, the term "sequential unit" or "sub-unit" will be defined as a moiety that is bound to other moieties of the same or a different kind to form a more complex molecule, such as oligonucleotides and peptide chains. It will further be appreciated that the term "open environment" will be defined as any environment which is not subjected to a closed or vapor saturated system to control evaporation of volatile solvents.

Attention is now directed to FIGS. 1 and 2 where a solid phase, micro-scale synthesis apparatus, generally designated 10, is shown for building molecules comprising sub-units through the application of the method and composition of the present invention by sequentially adding sub-units or sequential units to an open, solid support surface 11 in a liquid reagent solution 12. The synthesis apparatus, to be discussed in greater detail below, is configured to accurately deposit small or minute droplets 13 of reagent solution to functionalized binding sites 14 on the solid support surface 11 which are subjected to open environmental influences. In accordance with the present invention, the deposited reagent solution 12 includes chemical reactants contained in a high boiling point, polar, aprotic, organic solvents which facilitates the control of evaporation thereof during the chemical reaction. Unlike the prior art standard low boiling point solvents currently employed for open systems, these high boiling point solvents substantially reduce evaporation of the small reagent solution droplets from the exposed support surface 11 so that molecule growth, such as amidite coupling, can be completed. Thus, in an open environment, molecular synthesis can be more fully prolonged, while maintaining high reaction yields, without the need of either a closed or vapor saturated system to control evaporation of volatile solvents. As mentioned, once the solvents have evaporated, coupling reaction essentially ceases in the thick, gummy or crystalline residue.

In general, solvent systems developed for open environment molecular synthesis often involve relatively low boiling point solvents. Accordingly, by substituting these low boiling point solvents with relatively high boiling point solvents which exhibit similar solvent properties to the replaced solvents, to be discussed, the open environment reaction may be completed without the necessity of controlling evaporation of these solvents. While the present invention may be generally applied to any molecular synthesis where low boiling point solvents may be problematic in an open environment, the relatively high boiling point solvent substitution has been found particularly useful and beneficial for organic molecular synthesis and for biopolymers, such as oligonucleotides, peptides and peptide nucleic acids.

In the preferred form, the boiling point of the polar organic solvents is at least bout 140° C. at one (1) atmosphere (atm), as opposed to a lower boiling point of about 81° C. for the standard DNA solvent, acetonitrile. Thus, it will be appreciated that a relatively high boiling point will be defined as a boiling point of the solvent of at least About 140° C. at one (1) atm, while a relatively low boiling point will be defined as a boiling point of not more than about 100° C. at one (1) atm for the standard DNA solvents of acetonitrile, tetrahydrofuran, dimethoxyethane and nitromethane, as well as other low boiling point solvents such as ethanol, acetone and pyridine.

This higher boiling point assures that when minute or small volume droplets are applied in an open environment, typically in the size range of between about twenty (20) picoliters to about two (2) microliters, the droplets will not evaporate too quickly at normal ambient laboratory synthesis conditions in an open environment so that the chemical reaction can be prolonged or completed. Importantly, the lower vapor pressure of the high boiling point solvent when added in a mixture to a high vapor pressure solvent, tends to substantially lower the vapor pressure relative that of the prior art standard DNA solvents. Thus, high yield DNA synthesis can be completed before significant evaporative factors impede the chemical reaction.

Moreover, to promote a stepwise high coupling yield of at least about 97% (the conventional DNA standard), these high boiling point solvent systems preferably possess similar acidity, dielectric constant and solubility properties as that of the standard low boiling point solvent systems in current use. In accordance with the present invention, these higher boiling point solvents are not only less volatile than the standard solvents, but they include similar solvent properties which mimic the standard solvents so that substantially high reaction yields can be maintained. It has been found, for instance, that there are some high boiling solvent/activator combinations which provide high-yield amidite coupling similar to the acetonitrile/tetrazole pair, while also offering the reduced rate of evaporation necessary for surface array synthesis in small drops. The relative evaporation times of different candidate solvents compared to one standard DNA solvent, acetonitrile, have been significantly increased by a factor of at least about fifty (50).

The most preferred high boiling point, polar, aprotic, organic solvents have been determined to be from the group of dinitriles, specifically malononitrile, succinonitrile, glutaronitrile, adiponitrile and pimelonitrile. Compared to the low boiling point of acetonitrile (81° C.), the boiling point of these solvents is substantially higher at 218° C. for malononitrile, 265° C. for succinonitrile, 286° C. for glutaronitrile, 298° C. for adiponitrile and 310° C. for pimelonitrile. Hence, more preferably, the relative high boiling point will be at least about 200° C. at one (1) atm.

Moreover, the vapor pressures of these solvent systems are substantially lower than that of the more volatile standard DNA solvents (e.g., 70 mm of acetonitrile at room temperature). The vapor pressure and surface area to total volume ratio for a fifty (50) picoliter reagent solution droplet containing a solvent from the dinitrile group, hence, is significantly lower than that for a similarly sized droplet containing an acetonitrile solvent.

Accordingly, these solvents evaporate at a much slower rate at room temperature or standard synthesis environment. For instance, the evaporation half-life time of a 0.1 microliter drop of a dinitrile solvent is greater than about one (1) hour, as compared to about ten (10) seconds for acetonitrile. Hence, under a similar reaction environment, detrimental evaporative influences during polymer synthesis are less likely in the present invention.

Importantly and as set forth above, these solvent systems possess similar solvent properties as that of acetonitrile for the phosphoramidites such as acidity, viscosity, dielectric constant and solubility properties. For example, the group of dinitrile/acetonitrile analogues possesses a similar acidity to acetonitrile, and provides exceptionally high coupling yields (>99%) with the acid catalysts, such as tetrazole and S-ethyl tetrazole, and standard phosphoramidites. Adiponitrile or glutaronitrile with S-Ethyl tetrazole, as an acid catalyst, have been found to be the most preferred solvent/activator pairs.

The mononitrile group of the aprotic organic solvents have also been determined to substantially benefit small droplet polymer synthesis in open environments. These mononitriles solvents include: valeronitrile, having a high boiling point of 141° C.; capronitrile, having a high boiling point 163° C.; and benzonitrile, having a high boiling point 190° C. The vapor pressures of these mononitriles at room temperature are 5.0 mm, 1.0 mm and 0.5 mm, respectively, which is substantially lower than that of the standard DNA solvents. These mononitriles, hence, evaporate at a much slower rate at room temperature than acetonitrile, having an evaporation half-life time of a 0.1 microliter drop of greater than about one (1) hour.

While these mononitriles have been determined to be an inferior solvent for the phosphoramidites as compared to the dinitriles, probably due to their dominating alkyl residues, the mononitriles still possess similar solvent properties to acetonitrile for the phosphoramidites (e.g., acidity).

The polar, aprotic group of oxygenated solvents, such as diethlyene glycol dimethyl ether (diglyme), and triethylene glycol dimethyl ether (triglyme), have also been determined to be suitable high boiling point solvents for polymer synthesis. These oxygenated solvents provide good solubility for the phosphoramidites, as well, although are slightly more basic than the dinitriles. Accordingly, a more acidic catalyst is required to obtain higher coupling yields. One such acidic catalyst is pyridine hydrochloride (Py•HCl).

The boiling point of diglyme is 162° C., while that of triglyme is 216° C. Further, the vapor pressures of these oxygenated solvents at room temperature are 1.5 mm and 0.5 mm, respectively. Again, since the vapor pressure is lower than that of the standard DNA solvents, the evaporation half-life time of a 0.1 microliter drop is also longer than that of the standard DNA solvent. Coupling yields for these solvents have been greater than 98%.

Other high boiling solvents which yield good solubility for the phosphoramidites and more modest coupling yields with Py•HCl than those solvents described above are hexamethyl phosphoric triamide (HMPA), N-methyl pyrolidinone (NMP) and dimethylformamide (DMF). These solvents, however, may be better suited in combination with pyridine for the use with H-phosphonate coupling chemistry.

The method and solvent system of the present invention may also be employed with other organic synthesis in addition to DNA synthesis. As set forth in Example 2 below, high boiling point solvents can be utilized in combinatorial synthesis of amino acid hydroxamate derivatives as well which yielded a library of 500 different amino acid hydroxamate sulfonamide derivatives.

The present invention is particularly suitable for application with the delivery apparatus of Brennan, U.S. Pat. No. 5,474,796 (hereinafter, the '796 Patent) which is incorporated herein by reference in its entirety. Briefly, as shown in FIGS. 1 and 2, open, functionalized reactive sites 14 are defined or separated by non-reactive hydrophobic surface tension barriers, and specific reagents are delivered to the individual sites using drop-on-demand inkjet devices 15. Preferably, the size of each reactive or functionalized binding site 14 is typically about twenty (20) to about 2000 microns. Solutions of chemical reactants are delivered to the functionalized binding sites 14 on the support surface 11 through a piezoelectric or solenoid nozzle, or any other nozzles system capable of controllably dispensing small droplets accurately. The initial size of an ejected droplet is determined principally by the nozzle orifice diameter and the viscosity and surface tension of the liquid medium. The typical droplets 13 range in size from about twenty-five (25) to about 250 microns.

The reagent solution containing the chemical reactant and the high boiling point, polar, aprotic, organic solvent can be delivered to the functionalized binding site 14 through a piezo-electric pump (not shown) in an amount where the solution of chemical reactant at each binding site is separate from a reagent solution at other adjacent binding sites by surface tension. Briefly, in the piezo-electric pump, reagent solution is inserted through an inlet into a chamber formed between an upper plate and an opposed lower plate of the piezo-electric pump. Application of a voltage difference across the upper and lower plates causes compression of the piezo, forcing a micro-droplet of reagent solution out through the nozzle.

Figure 2A:
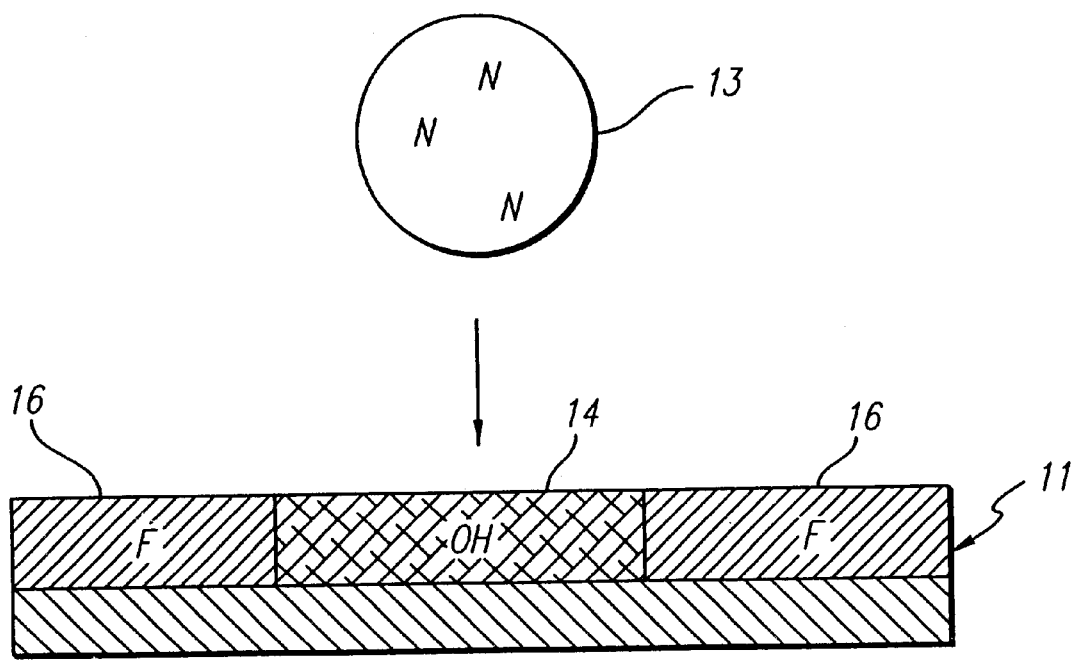
FIGS. 2A and 2B are enlarged side elevation views, in cross-section, of a support surface and a functionalized binding site illustrating the surface tension wall effect at the dot-interstices interface.
Figure 2B:
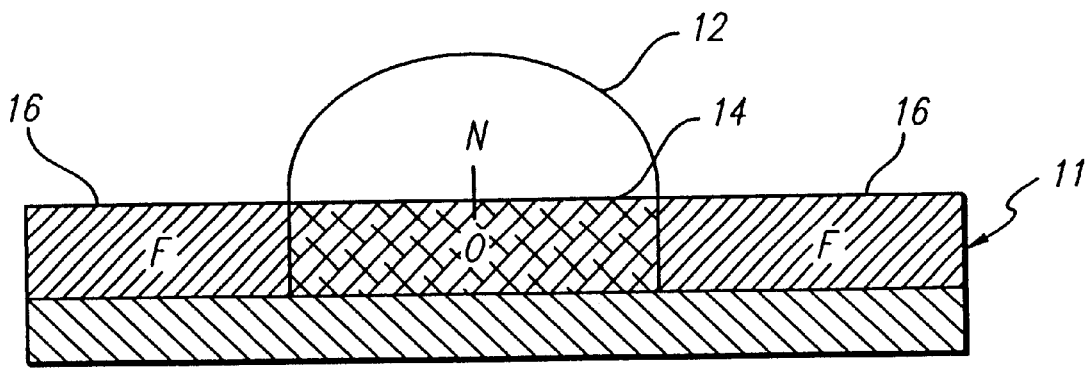

As best viewed in FIG. 2A, micro-droplet 13 of reagent solution is deposited on the functionalized binding site 14. Due to the differences in wetting properties of the reagent solution 12 on the functionalized binding site 14 and the surrounding surface 16 (FIG. 2B), the micro-droplet 13 of the reagent solution beads on the functionalized binding site 14 and the reactants in solution react with the solid support surface.

The piezoelectric pump that may be utilized in the invention delivers minute droplets 13 of liquid to the support surface 11 in a very precise manner. The picopump design is similar to the pumps used in ink jet printing, and is capable of producing fifty (50) micron or sixty-five (65) picoliter droplets at up to 3000 Hz.

From the above description of the present apparatus, it will be understood that the method of the present invention is provided for reducing evaporation of a liquid reagent solution during solid phase, micro-scale chemical synthesis of a molecule comprising sub-units on an open environment solid support surface 11. The method includes the steps of: (A) providing an open solid support surface 11 including at least one binding site 14 which is functionalized with a reactive chemical moiety. The next step includes: (B) depositing a substantially controlled and minute volume of liquid reagent solution 12 onto the support surface 11, and in contact with the binding site 14. In accordance with the present invention, the reagent solution includes reactants contained in at least one relatively high boiling point solvent, in contrast to standard organic solvents for such reagents. Such a high boiling point solvent substantially reduces evaporation of the reagent solution in the open environment during synthesis on the solid support 11 while maintaining a substantially high reaction yield.

The depositing step may be performed using drop-on-demand delivery of the reagent solution 12. This delivery may be provided through conventional delivery means or through a piezo-electric pump device 15, as long as the delivery volume, about twenty (20) picoliters to about two (2) microliters, is controlled and accurate. Further, the depositing step is further performed by discreet, stepwise synthesis at each the binding site by the phosphoramidite method or by the H-phosphomate method.

In another aspect of the present invention, and more particularly, a method of solid phase, micro-scale chemical synthesis of an oligonucleotide chain is provided on an open environment solid support surface. The method includes the steps of (A) providing an open solid support surface 11 including at least one binding site 14 which is functionalized with a reactive chemical moiety; and (B) depositing a substantially controlled and minute volume of liquid reagent solution 12 onto the support surface 11, and in contact with the binding site 14. In this embodiment, the reagent solution 12 includes reactants contained in a high boiling point, polar, aprotic organic solvent having a boiling point of at least about 140° C. This technique substantially reduces evaporation of the reagent solution in the open environment during oligonucleotide synthesis on the solid support while maintaining a substantially high coupling yield thereof.

Steps A and B may be repeated using the same or different chemical reactants to form at least one continuous oligonucleotide chain. When the open support surface 11 includes an array of functionalized reaction sites 14 (FIG. 1), the depositing step may be accomplished by individually depositing reagent solutions to selected reaction sites 14 of the array. Further, the depositing step may be accomplished by depositing the reagent solution to each selected reaction site 14 in an amount where the reagent solution at each reaction site 14 is separated from the reagent solution at other binding sites by surface tension. This may be performed by providing a support surface of each functionalized reaction site 14 which has a higher surface tension relative to the surrounding support surface 16 surrounding each functionalized binding site 14, which are preferably composed of non-reactive, hydrophobic materials.

The following examples serve to more fully describe the manner of using the above-described invention, as well as to set forth the best mode contemplated for carrying out various aspects of the invention. It is to be understood that this example in no way serves to limit the true scope of the invention, but rather are presented for illustrative purposes.

EXAMPLE 1

Oligonucleotide Synthesis on an Array Plate

Oligonucleotide synthesis was performed on a patterned glass array plate which provided functionalized aminoalkylsilane spots for synthesis separated by lipophilic fluoroalkylxysilanes. The array contained 500 spots with diameters of 0.5 mm. The array was synthesized, as described in the '796 Patent, using aminopropyl- and tetradecafluoro-1,1,2,2-tetrahydrooctyl siloxane for primary patterning.

Conversion of the short aminopropyl linker into the long-chain hydroxylalkyl linker was accomplished by treating the array with p-Nitrophenylchloroformate in dioxane:DCM (1:1) for 2 hours. Unreacted aminopropyl groups were capped using a 1:1 mixture of acetic anhydride and pyridine. The resulting carbamate intermediate was than converted into a hydroxyl bearing urea by reaction with 6-aminohexanol in acetonitrile overnight. A cleavable linker was synthesized by treating the patterned surface with 5'-DMT-nucleoside-3' succinate in acetonitrile utilizing TOTU as an activator for 2 hours.

Assembly of oligonucleotides on the so prepared spots was carried out according to the standard phosphoramidite procedure. Standard phosphoramidites and S-Ethyl tetrazole were dissolved in a mixture of adiponitrile (ADN) or glutaronitrile (GLN) and acetonitrile (ACN). The addition of a defined amount of the lower-boiling acetonitrile allowed the control of solvent viscosity and drop formation from the jet. A mixture of 90% ADN and 10% ACN proved optimal for drop formation and viscosity of the reagents.

Delivery of the appropriate protected nucleotides and activating reagents was directed to individual spots using a micropump apparatus as described in the '796 Patent. All other steps (e.g., DMT deblocking, washing) were performed on the array in a batch process by flooding the surface with the appropriate reagents. Reagents were then removed from the surface by spinning the array at high velocity.

After synthesis, the oligonucleotide was cleaved from the surface and deprotected by aqueous ammonia. The product (e.g., T10) was analyzed by HPLC and HPCE and showed a quality comparable or better than standard oligonucleotide synthesis on CPG. This leads to the conclusion that the stepwise synthesis yield was greater than about 98%.

EXAMPLE 2

Combinatorial Synthesis of Amino Acid Hydroxamate Derivatives

A patterned array was utilized as described in Example 1. Amino acids were first coupled to the array and then derivatized with different sulfonylchlorides to achieve diversity. Fmoc protected amino acids and activator (HATU) were dissolved in DMF:CH2CL2 (9:1). Both reagents were directed to single spots as described in the '796 Patent. After 15 minutes, the reagents were removed by spinning the array. After coupling, the array was washed with dichloroethane. Next the Fmoc protecting groups of the amino acids were removed by flooding the array surface with a 10% solution of piperidine in DMF for 10 minutes. After washing with DMF and THF, different sulfonyl chlorides dissolved in pyridine were directed to individual spots for derivatization. After a reaction time of 10 minutes, the reagents were removed by spinning and the array was washed with pyridine. After a final wash with pyridine, DMF, DMSO and DCE, the synthesized compounds were cleaved with 2M hydroxylamine in water/dioxane (1:7.5) for 48 hrs in a sealed chamber to yield a library of 500 different amino acid hydroxamate sulfonamide derivatives.

What is claimed is:

1. A method of reducing the evaporation of a liquid reagent solution during solid phase chemical synthesis of a molecule comprised of sub-units on an open environment solid support surface, said method comprising the steps of:

(a) providing an open solid support surface including at least one binding site which is functionalized with a chemical moiety; and (b) depositing a minute volume of liquid reagent solution onto said support surface and in contact with said binding site, said reagent solution including reactants contained in at least one polar and aprotic solvent having a boiling point of at least about 140° C., to reduce evaporation of the reagent solution during synthesis on said solid support.

2. The method according to claim 1 wherein said molecule is selected from the group consisting of nucleic acids, peptides and peptide nucleic acids.

3. The method according to claim 1 wherein said molecule is synthesized by sequentially adding sub-units thereto.

4. The method according to claim 1 wherein said depositing step is accomplished by individually depositing reagent solutions to said binding sites of said array.

5. The method according to claim 1 wherein said depositing step is performed by using drop-on-demand delivery of said reagent solution.

6. The method according to claim 5 wherein, said drop-on-demand delivery of said reagent solution is performed through an ink jet printing device.

7. The method according to claim 6 wherein said drop-on-demand delivery of said reagent solution is performed through a piezo-electric pump.

8. The method according to claim 1 wherein the reagent solution at said binding site is separated from the reagent solution at other binding sites by surface tension.

9. The method according to claim 1 wherein said functionalized binding site has a higher surface tension relative to the areas surrounding said functionalized binding site.

10. The method according to claim 9 wherein said areas surrounding said functionalized binding site are comprised of non-reactive materials.

11. The method according to claim 1 wherein the volume of the reagent solution is about 20 picoliters to about 2 microliters.

12. The method according to claim 1 wherein said open support surface is a glass surface.

13. The method according to claim 1 wherein the boiling point of said solvent is at least about 200° C.

14. The method of claim 1 wherein said solvent is selected from the group consisting of dinitriles, mononitriles, glymes, diglymes, triglymes, and trimethylphosphates.

15. The method according to claim 14 wherein said dinitriles include an acidity substantially similar to that of an acetonitrile solution.

16. The method according to claim 14 wherein said dinitriles are selected from the group consisting of succinonitrile, glutaronitrile, adiponitrile and pimelonitrile.

17. The method according to claim 14 wherein said mononitriles are selected from the group consisting of valeronitrile, benzonitrile and capronitrile.

18. A method of solid phase chemical synthesis of an oligonucleotide on an open environment solid support surface, said method comprising the steps of:

(a) providing an open solid support surface including at least one binding site which is functionalized with a chemical moiety; and (b) depositing a minute volume of liquid reagent solution onto said support surface and in contact with said binding site, said reagent solution including reactants contained in a polar and aprotic solvent having a boiling point of at least about 140° C., to reduce evaporation of the reagent solution during oligonucleotide synthesis on said solid support.

19. The method of oligonucleotide synthesis according to claim 18 wherein the boiling point of said solvent is at least about 200° C.

20. The method of claim 18 wherein said solvent is selected from the group consisting of dinitriles, mononitriles, glymes, diglymes, triglymes, and trimethylphosphates.

21. The method of oligonucleotide synthesis according to claim 20 wherein said dinitriles include an acidity substantially similar to that of an acetonitrile solution.

22. The method of oligonucleotide synthesis according to claim 20 wherein said dinitriles are selected from the group consisting of succinonitrile, glutaronitrile, adiponitrile and pimelonitrile.

23. The method of oligonucleotide synthesis according to claim 20 wherein said mononitriles are selected from the group consisting of valeronitrile, benzonitrile and capronitrile.

24. The method of oligonucleotide synthesis according to claim 18 wherein said depositing step is performed by using drop-on-demand delivery of said reagent solution.

25. The method of oligonucleotide synthesis according to claim 24 wherein said drop-on-demand delivery of said reagent solution is performed through a ink jet printing device.

26. The method according to claim 18 wherein the reagent solution at said binding site is separated from the reagent solution at other binding sites by surface tension.

27. The method of oligonucleotide synthesis according to claim 18 wherein said synthesis is performed by the phosphoramidite method.

28. The method of oligonucleotide synthesis according to claim 18 wherein said synthesis is performed by the H-phosphonate method.

29. A nucleoside reagent solution for oligonucleotide synthesis in minute volumes on an open environment solid support surface comprising:

a nucleotide reagent; and a polar and aprotic solvent having a boiling point of at least about 140° C. to reduce evaporation of the reagent solution during oligonucleotide synthesis.

30. The nucleoside reagent solution according to claim 29 wherein, the volume of the reagent solution is about 20 picoliters to about 2 microliters.

31. The nucleoside reagent solution according to claim 29 wherein the boiling point of said solvent is at least about 200° C.

32. The nucleoside reagent solution of claim 29 wherein said solvent is selected from the group consisting of dinitriles, mononitriles, glymes, diglymes, triglymes, and trimethylphosphates.

33. The nucleoside reagent solution according to claim 32 wherein said dinitriles include substantially similar acidity properties as that of an acetonitrile solution.

34. The nucleoside reagent solution according to claim 32 wherein said dinitriles are selected from the group consisting of malononitrile, succinonitrile, glutaronitrile, adiponitrile and pimelonitrile.

35. The nucleoside reagent solution according to claim 32 wherein said mononitriles are selected from the group consisting of valeronitrile, benzonitrile and capronitrile.

* * * * *